US009456893B2

(12) United States Patent
Ling

(10) Patent No.: US 9,456,893 B2
(45) Date of Patent: Oct. 4, 2016

(54) ENGINEERED TISSUE IMPLANTS AND METHODS OF USE THEREOF

(75) Inventor: Jian Ling, Spring Branch, TX (US)

(73) Assignee: SOUTHWEST RESEARCH INSTITUTE, San Antonio, TX (US)

(*) Notice: Subject to any disclaimer, the term of this patent is extended or adjusted under 35 U.S.C. 154(b) by 615 days.

(21) Appl. No.: 13/194,348

(22) Filed: Jul. 29, 2011

(65) Prior Publication Data

US 2013/0030548 A1    Jan. 31, 2013

(51) Int. Cl.
| A61F 2/02 | (2006.01) |
| C12N 5/071 | (2010.01) |
| C12N 5/0775 | (2010.01) |
| A61F 2/10 | (2006.01) |
| C12M 3/00 | (2006.01) |
| C12M 1/12 | (2006.01) |
| C12M 1/00 | (2006.01) |
| A61L 27/36 | (2006.01) |
| A61L 27/38 | (2006.01) |
| A61L 27/50 | (2006.01) |
| A61L 27/56 | (2006.01) |
| A61L 27/60 | (2006.01) |
| A61F 13/00 | (2006.01) |

(52) U.S. Cl.
CPC ............ *A61F 2/105* (2013.01); *A61L 27/3629* (2013.01); *A61L 27/3804* (2013.01); *A61L 27/3808* (2013.01); *A61L 27/3834* (2013.01); *A61L 27/507* (2013.01); *A61L 27/56* (2013.01); *A61L 27/60* (2013.01); *C12M 21/08* (2013.01); *C12M 25/14* (2013.01); *C12M 29/10* (2013.01); *A61F 13/00068* (2013.01)

(58) Field of Classification Search
CPC .......................... A61L 27/3808; A61L 27/507
See application file for complete search history.

(56) References Cited

U.S. PATENT DOCUMENTS

| 8,815,594 B2 | 8/2014 | Harris et al. |
| 9,044,530 B2 | 6/2015 | Ling et al. |
| 2008/0025956 A1 | 1/2008 | Yoder et al. |
| 2010/0168872 A1 | 7/2010 | Brown et al. |
| 2010/0279268 A1 | 11/2010 | Neumann et al. |
| 2011/0014597 A1 | 1/2011 | Frerich |
| 2011/0033927 A1 | 2/2011 | Rolle et al. |
| 2014/0161841 A1 | 6/2014 | Harris et al. |
| 2014/0170117 A1 | 6/2014 | Ling et al. |
| 2015/0050736 A1 | 2/2015 | Harris et al. |

OTHER PUBLICATIONS

Koch et al (Biomaterials. 2010: 31: 4731-4739).*
Linke et al (Tissue Engineering. 2007; 13(11): 2699-2707).*
Lange et al. (World J Gastroenterol. 2005; 11(29): 2297-4504).*
Kashfi et al. (Transplantation Proceedings. 2005; 37: 185-188).*
Chen, et al "Tissue Engineering of Cartilage Using a Hybrid Scaffold of Synthetic Polymer and Collagen." Tissue Engineering, vol. 10, No. 314 (2004) pp. 323-330.
Hokugo, et al "Preparation of Hybrid Scaffold From Fibrin and Biodegradable Polymer Fiber", Biomaterials, vol. 27 (2006), pp. 61-67.
Mikos, et al, "Preparation and Characterization of Poly(L-lactic acid)foams". Polymer, vol. 35, No. 5 (1994) pp. 1068-1077.
Liao et al, "Fabricaiton of Porous Biodegradable Polymer Scaffolds Using a Solvent Merging/Particulate Leaching Method.", Journal of Biomedical Materials Research, vol. 59, No. 4 (2001), pp. 676-681.
US Office Action issued in U.S. Appl. No. 13/720,543, mail dated Aug. 13, 2013 (15 pgs).
US Office Action issued in U.S. Appl. No. 13/712,583, mail dated Oct. 23, 2013 (12 pgs).
US Office Action, mail date Apr. 8, 2014 issued in U.S. Appl. No. 13/720,543 (12 pgs).
Baht, et al "Bone Sialoprotein-collagen Interaction Promotes Hydroxyapatite Nucleation"; Science Direct, Matrix Biology, vol. 27, 2008, pp. 600-608.
Rodrigues, et al "Characterization of a Bovine Collagen-hydroxyapaptite Composite Scaffold for Bone Tissue Engineering"; Biomaterials, vol. 24 (2003), pp. 4987-4997.
Auger, et al., "Tissue-engineered skin substitutes: from in vitro constructs to in vivo applications," Biotechnol. Appl. Biochem., 39. (2004) pp. 263-275.
Colton, "Implantable biohybrid artificial organs," Cell Transplant, vol. 4, No. 4. (1995) pp. 415-436.
Fizgerald, "Collagen in wound healing: are we onto something new or just repeating the past?" The Foot and Ankle Online Journal, 2(9):3 (2009).
Hirschi, et al., "PDGF, TGF-beta, and heterotypic cell-cell interactions mediate endothelial cell-induced recruitment of 10T1/2 cells and their differentiation to a smooth muscle fate," J Cell Biol, 141(3), (1998) pp. 805-814.

(Continued)

*Primary Examiner* — Scott Long
(74) *Attorney, Agent, or Firm* — Grossman, Tucker et al.

(57) ABSTRACT

A engineered tissue implant comprising a perfusion chamber formed with a biocompatible flexible tubular member having a wall defining an internal fluid flow passage and a porous scaffold within the fluid flow passage of the tubular member, the porous scaffold arranged such that, in a presence of a perfusion fluid, the perfusion fluid will flow through the porous scaffold and be inhibited from flow between the porous scaffold and the wall of the tubular member. The engineered tissue implant may be understood as a transplantable cell construct or as an implantable bioreactor for cell growth both in vitro and/or in vivo. A method to provide tissue for reconstruction may comprise forming the engineered tissue implant containing a scaffold, introducing and seeding cells to the scaffold, introducing a perfusion fluid to the scaffold which flows through the fluid flow passage and scaffold, proliferating the cells within the scaffold and forming blood vessels within the scaffold. This may be followed by transplanting the engineered tissue implant in vivo where nutrition and oxygen are provided to support the preloaded cells.

23 Claims, 8 Drawing Sheets

(56) References Cited

OTHER PUBLICATIONS

Kumar, et al., "Plastic surgery challenges in war wound," Advanced in Wound Care, 1, (2010) pp. 65-70.
Lantz, et al., "Small intestinal submucosa as a vascular graft: a review," J. Invest. Surg., 6(3), (1993) pp. 297-310.
Lockmic, et al, "An arteriovenous loop in a protected space generates a permanent, tightly vascular, tissue engieered construct," FASEB, 21(2). (2007) pp. 511-522.
Luo, et al., "A multi-step method for preparation of porcine small intestinal submucosa (SIS)," Biomaterials, 32, (2011) pp. 706-713.
Markowicz, et al., "Enhancing the vascularization of three-dimensional scaffolds: new strategies in tissue regeneration and tissue engineering," Topics in Tissue Engineering, vol. 2, Chapter 6, \Eds. Ashammakhi N Reis RL.—2005 (15 pages).
Moon, et al., "Vascularization of engineered tissues: approaches to promote angiogenesis in biomaterials," Current Topics in Medicinal Chemistry, 8(4), (2008) pp. 300-310.
Nillesen, et al., "Increased angiogenesis and blood vessel maturation in acellular collagne-heparin scaffolds containing both FGF2 and VEGF," Biomaterials, 28, (2007) pp. 1123-1131.
Paige, et al., "Engineering new tissue: formation of neocartilage," Tissue Eng., 1, (1995) pp. 97-106.
Park, et al., "Tissue engineering of urinary organ," Yonsei Med. J., 41, (2000) pp. 780-788.
Raghavan, et al., "Physical characteristics of small intestinal submucosa scaffolds are location dependent," J. Biomed. Mater. Rec. A, 73, (2005) p. 90-96.
Ratcliffe, "A Tissue engineering of vascular grafts," Matrix Biol., 19, (2000) pp. 353-357.
Roeder, et al., "Compliance, elastic modulus, and burst pressure of small-intesine submucosa (SIS), small-diameter vascular grafts," J. Biomed Mater Res, 45.—(1999) p. 65-70.
Sakiyama-Elbert, et al, "Development of fibrin derivatives for controlled release of heparin-binding growth factors," J. Control. Release, 65, (2000) pp. 389-402.
Tsigkou, et al., "Engineered vascularized bone grafts," PNAS, 107(8), (2010) pp. 3311-3316.
Wang, et al., "Osteogenesis and angiogenesis of tissue engineered bone construct by prevascularized β-tricalcium phosphate scaffold and mensenchymal stem cells," Biomaterials, 31, (2010) pp. 9452-9461.
V.Cannillo, et al, "Fabrication of 45S5 Bioactive Glass-Polycaprolactone Composite Scaffolds"; 17th International Conference on Composite Materials (ICCM-17), Edinburgh (UK), Jul. 27-31, 2009 (downloaded Jul. 19, 2012 http://www.iccm-central.org/Proceedings/ICCM17proceedings/Themes/Applications/BIOMEDICAL%20APPLICATIONS/B1.5A%20Cannillo.pdf).
B. Slaughter, et al, "Hydrogels in Regenerative Medicine"; Advanced Materials 2009, vol. 21, pp. 3307-3329.
D. Yu, et al, "Bladder Wall Grafting in Rats Using Salt-modified and Collagen-coated Polycaprolactone Scaffolds: Preliminary Report"; International Journal of Urology (2007) vol. 14, pp. 939-944.
H. Lee et al, "Designed Hybrid Scaffolds Consisting of Polycaprolactone Microstrands and Electrospun Collagen-Nanofibers for Bone Tissue Regeneration"; Journal of Biomedical Materials Research, Applied Biomaterials/ vol. 97B, Issue 2, (online Mar. 7, 2011—pp. 263-270).
Clarke, Bart , "Normal Bone Anatomy and Physiology", Clinical Journal of the American Society of Nephrology, vol. 3, 2008, S131-S139.
Colfen, Helmut , "A Crystal-Clear View", Nature Materials, News & Views; vol. 9 Dec. 2010, 960-961.
Du, C. et al., "Formation of Calcium Phosphate/Collagen Composites Through Mineralization of Collagen Matrix", John Wiley & Sons, Inc. 2000, 518-527.
Gower, Laurie B. , "Biomimetic Model Systems for Investigating the Amorphous Precursor Pathway and Its Role in Biomineralization", 2008 American Chemical Society, Chem, Rev 2008, 108, 2008, 4551-4627.
Huang, Zhi et al., "A Bone-like Nano-hydroxyapatite/collagen Loaded Injectable Scaffold", IOP Publishing, Biomedical Materials, Biomed Mater, 4, 2009, 1-7.

Kikuchi, Masanori et al., "Self-organization Mechanism in a Bone-like Hydroxyapatite/collagen Nanocomposite Synthesized In Vitro and Its Biological Reaction In Vivo", Elsevier, Biomaterials 22 (2001), 1705-1711.
Lees, Sidney et al., "A Study of Some Properties of Mineralized Turkey Leg Tendon", 1992 Gordon and Breach Science Publishers S.A.; Connective Tissue Research 1992, vol. 28, 1992, 263-287.
Lickorish, David , "Collagen-hydroxyapatite Composite Prepared by Biomimetic Process", Wiley Periodicals, Inc., J. Biomed Mater Res, 2003, 19-27.
Olszta, Matthew J. et al., "Bone Structure and Formation: a New Perspective", Elsevier, Science Direct; Reports: A Review Journal, Materials Science and Engineering, R 58, 2007, 77-116.
Ozawa, Hidehiro et al., "Current Concepts of Bone Biomineralization", J. Oral Bioscience, 50(1), 2008, 1-14.
Pek, Y.S. et al., "Porous Collagen-apatite Nanocomposite Foams as Bone Regeneration Scaffolds", Elsevier Biomaterials 29, 2008, 4300-4305.
Prosecka, E. et al., "Optimized Conditions for Mesenchymal Stem Cells to Differentiate Into Osteoblasts on a Collagen/hydroxyapatite Matrix", Wiley Periodicals, Inc., Society for Biomaterials, J. Biomed Mater Res Part A 2011:99A, 2011, 307-315.
Thula, Taili T. et al., "In Vitro Mineralization of Dense Collagen Substrates: A Biomimetic Approach Toward the Development of Bone-graft Materials", Elsevier, Science Direct; Acta Biomaterialia, Inc. 7, 2011, 3158-3169.
Viguet-Carrin, S. et al., "The Role of Collagen in Bone Strength", Osteoporos International (2006) 17, Dec. 9, 2005, 319-336.
Yamauchi, Kiyoshi et al., "Preparation of Collagen/Calcium Phosphate Multilayer Sheet Using Enzymatic Mineralization", Elsevier Ltd., Biomaterials, 2004, 5481-5489.
Antebi, et al "Biomimetic Collagen-Hydroxyapaptite Composite Fabricated Vla a Novel Perfusion-Flow Mineralization Technique"; Tissue engineering Part C, vol. 19, No. 7 (online ahead of editing Nov. 16, 2012) pp. 487-496.
Sikavitsas, et al "Mineralized Matrix Deposition by Marrow Stromal Osteoblasts in 3D Perfusion Culture Increases With Increasing Fluid Shear Forces."; Proceedings of the National Academy of Sciences, vol. 100, No. 25 (Dec. 9, 2003) pp. 14683-14688.
Badylak, et al, "Extracellular Matrix as a Biological Scaffold Material: Structure and Function"; ScienceDirect, Acta Biomaterialia, vol. 5, 2009, pp. 1-13.
Cartmell, et al; "Effects of Medium Perfusion Rate on Cell-Seeded Three-Dimensional Bone Constructs In Vitro"; Tissue Engineering, vol. 9, No. 6 (2003), pp. 1197-1203.
Praetorius, et al; "Bending the MDCK Cell Primary Cilium Increases Intracellular Calcium"; Journal of Membrane Biology, vol. 184, 2001, pp. 71-79.
Karperien, et al; "Morphogenesis, Generation of Tissue in the Embryo"; Elsevier/Academic Press, Tissue Engineering, Senior Editor C.vanBlitterswijk; 2008 San Diego, CA, Book Publication Info and pp. 58-62.
US Office Action issued in U.S. Appl. No. 13/720,543, mail dated Sep. 23, 2014 (11 pgs).
Thula et al, "Mimicking the Nanostructure of Bone: Comparison of Polymeric Process-Directing Agents". Polymers, 2011, vol. 3, Dec. 27, 2010, pp. 10-35.
US Office Action issued in U.S. Appl. No. 14/467,879, mail date Jun. 2, 2015 (13 pgs).
Chen, et al; "Extracellular Matrix Made by Bone Marrow Cells Facilitates Expansion of Marrow-Derived Mesenchymal Progenitor Cells and Prevents Their Differentiation Into Osteoblasts"; Journal of Bone and Mineral research, vol. 22, No. 12, 2007 pp. 1943-1956.
Jiao, et al: "Fabrication and Characterization of PLLA-chitosan Hybrid Scaffolds With Improved Cell Compatibility"; InterScience, Journal of Biomedical Materials Research Part A, vol. 80A, No. 4 (online Oct. 20, 2006) pp. 820-825.
Lai, et al; "Reconstitution of Marrow-Derived Extracellular Matrix Ex Vivo: A Robust Culture system for Expanding Large-Scale Highly Functional Human Mesenchymal Stem Cells"; Stem Cells and Development, vol. 19, No. 7, 2010, pp. 1095-1108.
Wang, et al; "A Hybrid Scaffold of Poly(Lactide-CO-Glycolide) Sponge Filled With Fibrin Gel for Cartilage Tissue Engineering"; Chinese Journal of Polymer Science, vol. 29, No. 2, 2011, pp. 233-240.

\* cited by examiner

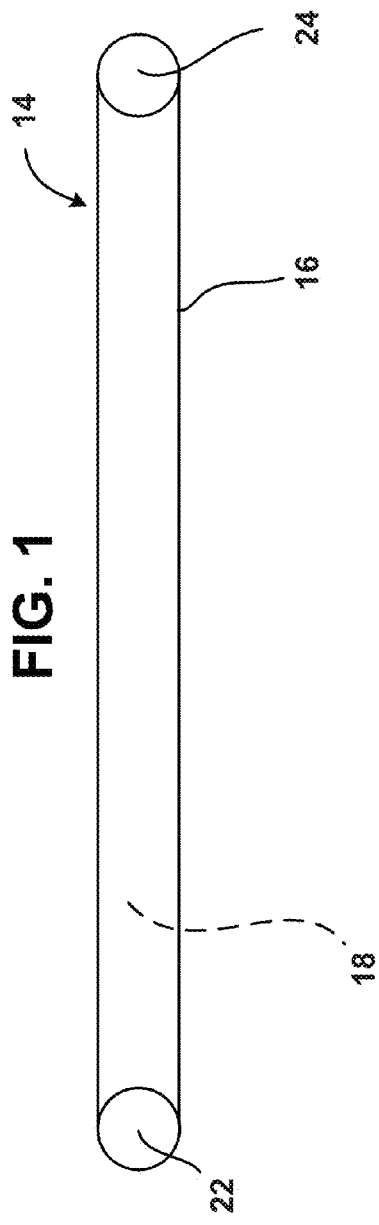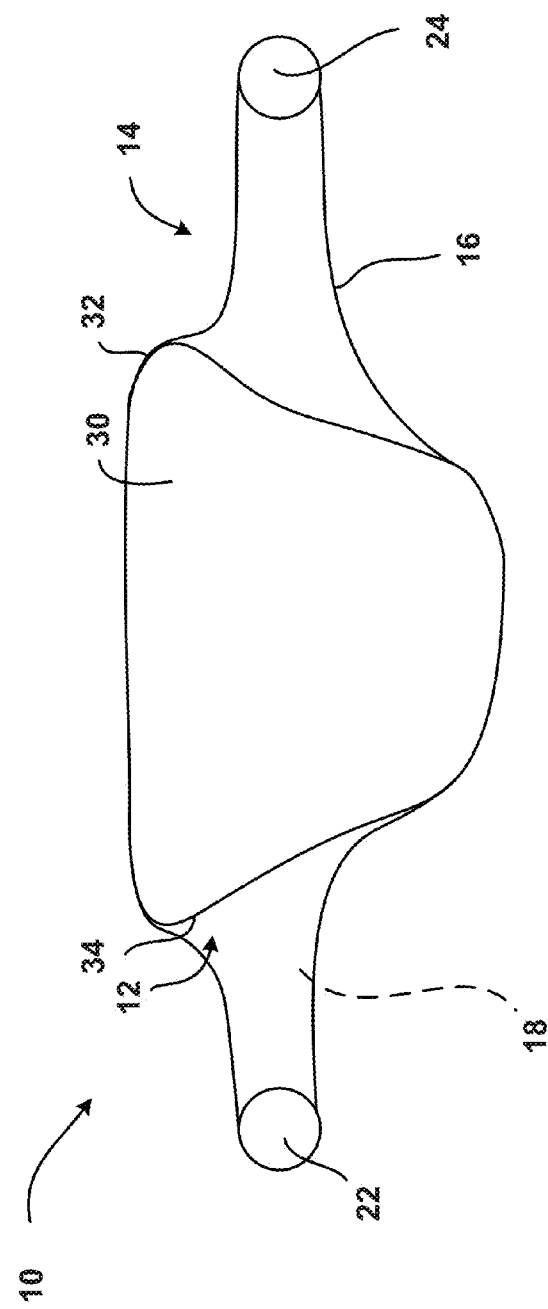

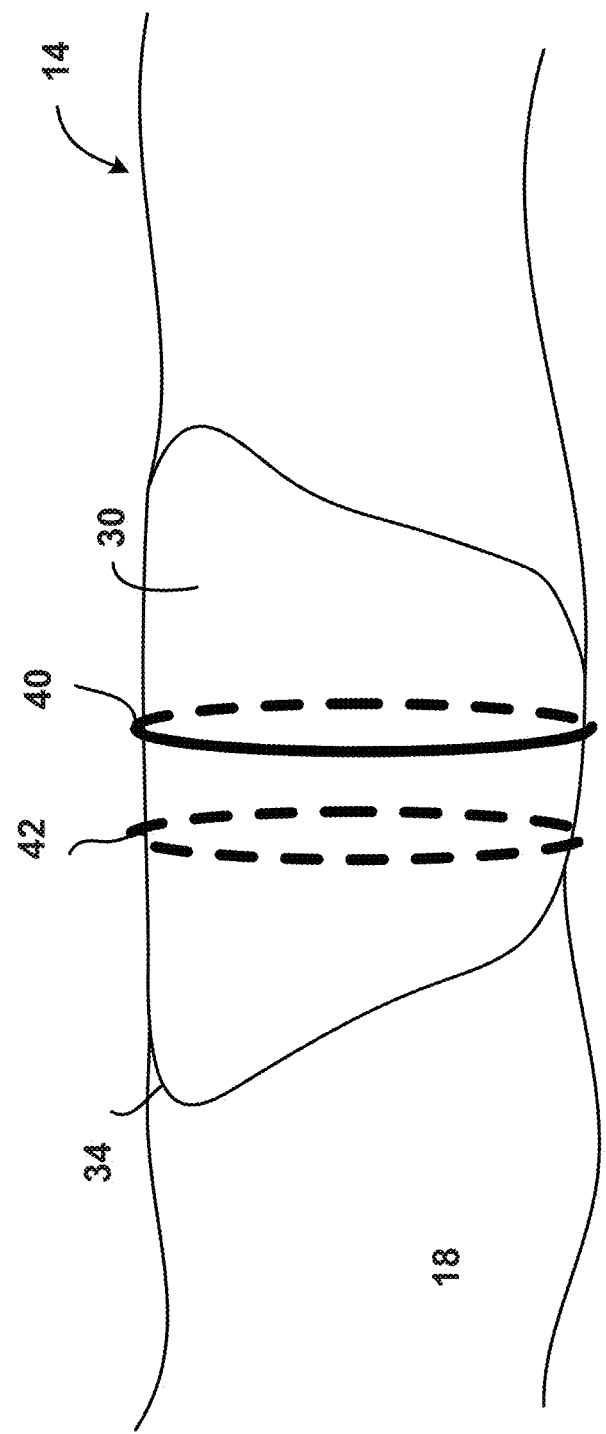

ENGINEERED TISSUE IMPLANTS AND METHODS OF USE THEREOF

FIELD OF THE INVENTION

The present disclosure relates to engineered tissue implants, and more particularly an engineered vascularized tissue implants and methods of for use thereof, particularly for wound healing. The engineered tissue implant may be understood as a transplantable cell construct or as an implantable bioreactor for cell growth both in vitro and/or in vivo.

BACKGROUND

Wound healing may be understood to occur in four phases: (1) Inflammation and hemostasis, (2) proliferation, (3) remodeling, and (4) epithelialization. Inflammation may be understood to initiate with an injury itself. Due to the disrupted blood vessel(s), bleeding may result in the release of (a) platelets to form clot(s) and inhibit bleeding, (b) white blood cells to clear wound debris, and (c) proteases/collagenases to degrade wounded portions of the extracellular matrix. In the proliferation phase, endothelial cells may be understood to migrate from nearby intact venules and start proliferation to form new vessels that supply the rebuilding cells with oxygen and nutrients. In this period, stem cells and fibroblasts may be recruited to the wound site to produce a new extracellular matrix framework, primarily collagen. In the next remodeling phase, the strength of collagen framework may be enhanced. In the final epithelialization phase, a new skin may be formed.

Important aspects of the wound healing process include re-vascularization and collagen deposition. Re-vascularization, or neoangiogenesis, to re-establish tissue perfusion and supply nutrition and oxygen to the wound bed may be understood as the foundation of the wound healing process. Anti-bacterial lymphocytes do not work well to clear the wound sites in hypoxic environment. Furthermore, oxygen supply may be understood to be critical for the increase of cell metabolism to synthesize and deposit collagen to fill the wound defects. Moreover, wound closure through collagen deposition may aid the healing process and protect against invading pathogens, as a wound may not have an effective skin barrier to act as a first line of defense.

Wounds which may be considered particularly difficult to heal include chronic wounds and combat wounds. Chronic wounds represent a significant and growing challenge to our healthcare system. Chronic wounds, such as venous leg ulcers, pressure ulcers, and foot ulcers in diabetic patients, often fail to achieve adequate healing. Failure to achieve adequate healing is often related to tissue ischemia due to poor local blood supply. These chronic wounds may be seen in ambulatory wound care centers with frequent recurrences yet less satisfactory outcomes, and therefore need long term care, resulting in growing utilization of health care resources. If tissue ischemia and hypoxic condition could be altered regionally, an increased healing rate could be achieved. For example, nitric oxide presented at wound sites may send a vasodilatation signal which results in an increase of local blood flow and the acceleration of collagen synthesis and wound closure. Similarly, studies indicated that the application of aloe vera at the wound sites also promotes blood flow and results in an increased oxygen supply.

Combat wounds, such as those due to high energy blasts, may be characterized by severe composite tissue damage, large zones of injury, and extensive vascular disruption. Due to the difficult closure of these large wounds, one of the most serious complications of these wounds may be infection. Consequently, the longer the wound is open, the more difficult it often may be for the wounds to heal. When a damaged area becomes infected, the infection may be understood to stop the healing process and can even cause poisoning and death. Optimal care and reconstruction of these massive soft tissue and bone defects of the extremities and craniofacial skeleton has yet to be adequately defined.

Tissue transplantation may be one treatment used to augment deficient tissue in the region of injury and therefore cover the large area of wounds. One tissue transplantation procedure in craniofacial and extremity wounds may involve microsurgical free flap reconstruction. This procedure may be understood to completely detach skin, fat, and blood vessels (arteries and veins), called a flap, from one part of the body and move them to the wound sites. The flap may then be reattached, with the arteries and veins of the flap reconnected to the arteries and veins near the wound sites. However, free flap reconstruction is limited by the availability of the tissue flaps from either autograft or allograft due to the donor-site morbidity. Thus, while free flap reconstruction may be used in the treatment of chronic and combat wounds, such reconstruction is somewhat limited.

Tissue engineering and regenerative medicine may also be used for treating traumatic tissue damage and loss. Engineered tissue scaffolds may include natural and synthetic materials such as collagen, hydroxyapatite (HA) and PLGA. Collagen-based acellular scaffolds may be particularly used for wound treatment. Three-dimensional scaffolds may not only provide coverage over soft tissue deficit to reduce the risk of contamination and subsequent infection, but also may regulate MMP (matrix metalloprotease) levels to promote normal progression through the stages of wound healing. In comparison with acellular scaffolds, scaffolds pre-loaded with tissue specific cells and stem cells, which may be referred to as cell constructs, have a better chance to mimic functionality and complexity of native tissue, and thus achieve a better and faster wound treatment.

Engineered cell constructs may be used to repair cartilage, skin, urethra, and blood vessels. However, the success of these constructs in vivo is understood to be mainly due to their low thickness, where oxygen and nutrients can diffuse into the constructs and sustain cellular viability. However, as the constructs become larger and thicker, cells located more than 200 to 300 µm away from nearest capillaries may be understood to suffer from hypoxia and apoptosis following the implantation. It usually takes days or even weeks before the host's vasculature can grow into the constructs to feed the cells inside the constructs. At that time most of the preloaded cells on the constructs will die. Therefore, the implantation of cell constructs for wound repair remains a challenge.

Attempts have been made to get blood supply close to cell constructs after implantation. One attempt was to form an open groove in an outer surface of a tricalcium phosphate scaffold and thereafter a nearby artery and vein of the host was inserted into the groove of the scaffold after it was implanted. Another attempt was to place a cell construct inside a rigid, (inflexible) chamber. A nearby artery and vein was then sutured to the chamber to supply blood to the scaffold in what may be referred to as an arteriovenous (AV) loop. The concept of an AV loop derives from the free flap reconstruction technique used in clinics. Although both examples may increase of local perfusion to the scaffolds, they have several problems. First, both are still diffusion models, as there are no integrated vascular paths that can directly connect to blood supply to deliver blood to the cells deep inside the scaffold upon the implantation. Second, in the case of the rigid chamber, the chamber actually prevents the cell construct from fully interacting with surround tissues and finally integrating into the existing tissue to reach the goal of wound healing. Third, the rigid chamber is not easy to adapt to different shapes of constructs.

Thus, while engineered "tissue flaps" may be used for wound care, the survival of the cell construct after implanted in vivo remains a challenge, particularly due at least in part to perfusion and associated hypoxia.

SUMMARY

The present disclosure relates to transplantable engineered tissue implants that can be vascularized or even pre-developed into functional tissue in vitro and then transplanted in vivo as engineered "tissue flaps" for wound treatment. The engineered tissue implant may be understood as a transplantable cell construct or as an implantable bioreactor for cell growth both in vitro and/or in vivo. The engineered tissue implants are configured to connect with host blood vessels in vivo to supply oxygen and nutrition to cells thereof immediately after the implantation. The engineered tissue implants are also configured to integrate into surrounding host tissue to achieve wound healing.

An engineered tissue implant may include a three-dimensional (3D) scaffold within a flexible perfusion chamber. The engineered tissue implant may comprise a same or similar tissue type as the lost tissue at a wound site, and may be hand shapeable as to conform to the anatomical shape of the wound site. The flexible perfusion chamber may allow the scaffold to be perfused in vitro as well as in vivo after transplantation. The engineered tissue implant may be perfused in vivo with an arteriovenous (AV) loop in the host.

A capillary network may be established in the engineered tissue implant in vitro by the co-culture of endothelial cells and mesenchymal stem cells (MSCs) in the construct, with a supplement of vascularization growth factors, and under continuous perfusion by an in vitro bioreactor. Furthermore, the engineered tissue implants may be developed into functional tissue types such as muscle, bone, cartilage, and epithelial in vitro.

The engineered tissue implants may accelerate the wound healing process since they are able to: 1) cover the wound site to keep the wound moist and to reduce the risk of infection; 2) reduce tissue regeneration time through the incorporation of functional tissue developed in vitro; 3) provide additional blood supply to the wound sites to promote all phases of wound healing process; and 4) provide a source of stem cells to the wound sites for tissue regeneration.

In one exemplary embodiment, the present disclosure provides a engineered tissue implant comprising a perfusion chamber formed with a flexible tubular member having a wall defining an internal fluid flow passage; and a porous scaffold within the fluid flow passage of the tubular member, the porous scaffold arranged such that, in a presence of a perfusion fluid, the perfusion fluid will flow through the porous scaffold and be inhibited from flow between the porous scaffold and the wall of the tubular member.

In another exemplary embodiment, the present disclosure provides a method to provide tissue for reconstruction may comprise forming the engineered tissue implant; introducing and seeding cells to the scaffold; introducing a perfusion fluid to the scaffold which flows through the fluid flow passage and scaffold; proliferating the cells within the scaffold; and forming blood vessels within the scaffold.

FIGURES

The above-mentioned and other features of this disclosure, and the manner of attaining them, will become more apparent and better understood by reference to the following description of embodiments described herein taken in conjunction with the accompanying drawings, wherein:

FIG. 1 illustrates a tubular member which may be used with an engineered tissue implant according to the present disclosure;

FIG. 2 illustrates an engineered tissue implant according to the present disclosure;

FIG. 4 illustrates other embodiments of an engineered tissue implant according to the present disclosure;

DETAILED DESCRIPTION

Figure 3:
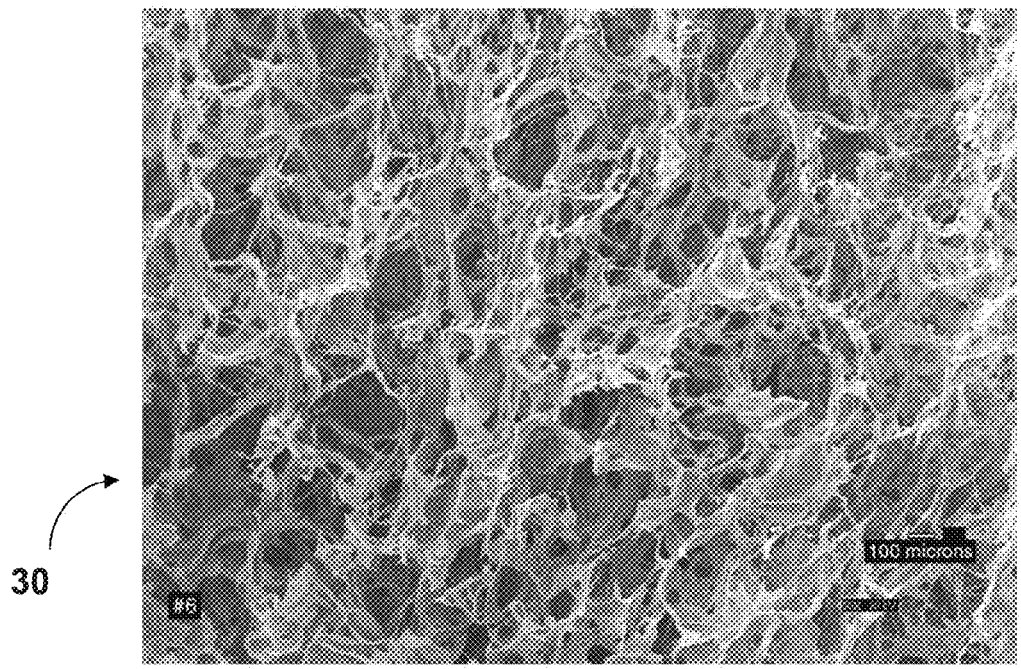
FIG. 3 illustrates a porous tissue engineering scaffold according to the present disclose having pores which are interconnected to provide tortuous passages.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

Referring now to FIGS. 1 and 2, there is illustrated an engineered tissue implant 10 according to the present disclosure. The engineered tissue implant may be understood as a transplantable cell construct or as an implantable bioreactor for cell growth both in vitro and/or in vivo. Engineered tissue implant 10 may comprise a perfusion chamber 12 formed with an elongated hollow tubular member 14 having a tubular wall 16 defining a tubular fluid flow passage 18, as well as a fluid inlet opening 22 and an opposing fluid outlet opening 24. In certain embodiments, the tubular member 14 may have a cylindrical tubular wall 16 defining a cylindrical tubular passage 18 and a circular inlet opening 22 and a circular outlet opening 24. More particularly, tubular member 14 may comprise a flexible, resilient (elastic) thin-wall tube with a lumen thereof providing the tubular passage 18. As used herein, a tubular member may be understood to be flexible if it is capable of being bent repeatedly without significant injury or damage and be conformable to the tissue reconstruction site of a recipient host.

Tubular member 14 may be naturally formed or man-made from natural or synthetic materials. Tubular member 14 may have a thickness in a range of and including all increments between $10^{-3}$ millimeters to 10 millimeters more particularly a thickness in the range of and including all increments between 0.05 millimeters to 1.0 millimeters.

A naturally formed tubular member 14 may be derived from the intestinal tract (large or small intestine) of an animal, such as a cultivated animal or a human being (e.g. particularly from a cadaver). As used herein, the term "animal" includes any member of the kingdom Animalia, which should be understood to include human beings. Cultivated animals may include laboratory animals and domesticated animals such as farm animals and livestock which may further include porcine/pig/swine, sheep, goat, house, steer and other cattle. As used herein a cultivated animal includes any animal raised, domesticated or otherwise kept by a human being for a particular purpose, such as the advancement of medicine.

A naturally formed tubular member 14 may also be derived from other naturally formed tubular passages of an animal, including blood vessels such as veins and arteries. More particularly, tubular member 14 may be made of decellularized intestinal tract, blood vessels and other tubular passages of a human or animal. For example, a naturally formed tubular member 14 may be comprised sub-mucosa, a layer of the intestine that consists mainly of naturally occurring collagen. Such may include decellularized small intestine submucosa (SIS), particularly porcine.

Decellularized porcine small intestine submucosa (SIS) is composed mainly of collagen, and may possess wall compliance and mechanical strength similar to host vessels. Decellularized porcine small intestine submucosa (SIS) may have a transparent or translucent flexible wall. Decellularized porcine SIS may be obtained from Cook Biotech (West Lafayette, Ind.), commercially available sausage skin, or fresh intestine cleaned and decellularized following known protocol. Fresh porcine small intestine may be obtained from Innovative Research (Novi, Mich.) or a slaughterhouse.

A man-made tubular member 14 may be formed by a manufacturing process, such as by extrusion. Man-made tubular member 14 may be made of collagen, cellulose, or other biocompatible materials like polymers and copolymers of the hybrid of several different materials. Collagen for a man-made tubular member 14 may be derived from the skins/hides, bones and tendons of animals (e.g. porcine).

Tubular member may also be formed by any natural or synthetic sheet-like materials that are biocompatible. The examples are skin of human or animal. The tubular membrane may be formed by wrapping around the three dimensional tissue engineering scaffold 30 and bond by biocompatible adhesives or suture.

As shown in FIG. 2, a three dimensional tissue engineering scaffold 30 may be located within tubular passage 18 of tubular member 14, particularly by elastically deforming (stretching) tubular member 14 as to insert scaffold 30 within tubular passage 18 through inlet or outlet opening 22, 24.

Scaffold 30 may comprise of natural materials such as collagen, fibrin, hydroxyapatite (HA), glycosaminoglycans (GAG), hyaluronic acid, and their composites. Scaffold 30 may also comprise of biocompatible synthetic materials such as PLGA (poly(lactic-co-glycolic acid)), PLLA (poly (L-lactic acid)), PLA (polylactic acid), PGA (polyglycolic acid), PCL (polycaprolactone), and their composites. Scaffold 30 may also comprise of other biocompatible materials like stainless steel, titanium alloy, and ceramics. Scaffold 30 may also comprise of natural scaffold like decellularized bone of human and animal. Scaffold 30 may also be a piece of tissue from a human or an animal.

The type of material selected for scaffold 30 may ultimately depend on the application. For example, a collagen-based scaffold 30 may be more suitable for soft tissue reconstruction and wound healing, while a hydroxyapatite-based scaffold 30 may be more suitable for hard tissue reconstruction and wound healing, such as repairing bone defects.

Referring to FIG. 3, the scaffold 30 may comprise a plurality of interconnected pores and tortuous passages, which is permeable to a flow of perfusion fluid there through, as set forth in greater detail below. The porous structure may therefore facilitate the delivery of nutrition and oxygen to the cells therein, throughout the scaffold 30, after transplantation. It may be appreciated that such functionality supports the survival and proliferation of the cells therein after transplantation and provides for a successful engineered tissue implant.

The porous structure may have an average pore size (as determined, for example, by average cross-sectional dimension such as diameter) in the range of and including all increments between 1 micron (micrometers) to 1000 microns, and more particularly an average pore size in the range of and including all increments between 100 microns to 500 microns. Even more particularly, porous structure may have an average pore size of 300 microns.

The porosity of the porous structure, as defined by the pore volume over the total volume of the structure, may be greater than or equal to 50 percent (e.g. in the range of an including all increments between 50 percent to 99 percent), and more particularly greater than or equal to 75 percent (e.g. in a range of and including all increments between 75 percent to 95 percent). Even more particularly, the porous structure may have a porosity greater than or equal to 85 percent (e.g. in a range of and including all increments between 80 percent to 95 percent).

To provide a scaffold 30 having increased conformance to dimension/shape of tissue loss at a tissue reconstruction site, such as a wound site, of a host, a three dimensional mold of suitable dimension and shape may be designed with suitable computer software (e.g. Solid Works) and prototyped in a polymer such as acrylonitrile-butadiene-styrene (ABS) using a three dimensional printer. The scaffold 30 may then be fabricated from the three dimensional mold. As shown in FIG. 2, for example, scaffold 30 may, for example, have a conical shape, which may be used for tissue reconstruction of, for example, a bullet or shrapnel wound.

To fabricate a scaffold 30 with proper porosity, a freeze-drying method may be used in which uses a controlled freezing process to form ice crystals inside the scaffold material. The frozen material subsequently goes through a freeze-drying (or lyophilization) process to sublimate the ice out of the collagen leaving a porous structure. The pore size is determined by the ice crystal size which is dependent on the endpoint freezing temperature. The fabrication of porous scaffold may also used solvent casting and particulate leaching method, gas foaming method, and micro-fabrication method.

The tubular member 14 may be arranged around the scaffold 30 as to form an interference and compression fit at an interface 32 between tubular member 14 and scaffold 30, such that, in a presence of a perfusion fluid, the perfusion fluid will flow through the porous scaffold 30 and be inhibited from flow between the porous scaffold 30 and the wall 16 of the tubular member 14. More particularly as shown in FIG. 2, scaffold 30 has an outer periphery 34 surrounded in an enclosed ring pattern by a portion of the wall 16 of tubular member 14.

Scaffold 30 may be compression fit within tubular passage 18 of tubular member 14 such that tubular wall 16 of tubular member 14 contacts scaffold 30 and places a compressive force on scaffold 30. More particularly, the compressive force placed on scaffold 30 may be due to stretching of the tubular member 14 and a force of elastic recovery of tubular member 14 in response to stretching and elastic deformation thereof when scaffold 30 is introduced to tubular member 14. In other words, when scaffold 30 is fit within tubular member 14, tubular member 14 may be stretched and elastically deformed around scaffold 30.

As such, the tubular member 14 may place a compressive (hoop) force on the scaffold 30 in response to the tubular member 14 being in a stressed/stained state and unable to return to its previous (unstressed/unstrained) state. Now, while tubular member 14 may place a compressive force on the scaffold 30, the force should not be significant enough to collapse the scaffold 30 such that tissue scaffold 30 is crushed and unable to function as such.

It may be appreciated that different materials for scaffold 30 may be expected to exhibit different stiffness/compressive strength relative to one another. For example, a scaffold 30 of hydroxyapatite (HA) may have a greater stiffness and resistance to compression (compressive strength) than a scaffold 30 of collagen. However, it may be possible to increase the stiffness and resistance to compression of a collagen scaffold 30 by, for example, crosslinking and/or controlled mineralization technology to enhance the mechanical strength thereof.

To further protect a scaffold 30, such as a collagen scaffold, from being collapsed upon introduction to tubular member 14, alternative methods of integrating/assembling the scaffold 30 and the tubular member 14 may be utilized. For example, as shown in FIG. 4, rather than relying upon a compression fit between the scaffold 30 and tubular member 14, the scaffold 30 and tubular member 14 may be adhesively joined/bonded together with a suitable adhesive 40, such as fibrin glue, applied to scaffold 30 in an enclosed ring pattern. As a result, upon assembly of tubular member 14 and scaffold 30, the adhesive 40 may be located at the interface 32 between tubular wall 16 and scaffold 30. In this manner, a tubular member 14 with a larger diameter passage 18 may be utilized than with the compression fit.

In yet another alternative methods of integrating/assembling the scaffold 30 and the tubular member 14, as shown in FIG. 4, the scaffold 30 and tubular wall 16 may be mechanically joined after assembly, such as by suture 42, applied in an enclosed ring pattern. Again, in this manner, a tubular member 14 with a larger diameter passage 18 may be utilized than with the compression fit. The foregoing methods may provide a seal at the interface between tubular member 14 and scaffold 30, and inhibit a perfusion fluid from flowing around the scaffold 30 rather than through the scaffold 30.

Figure 6:
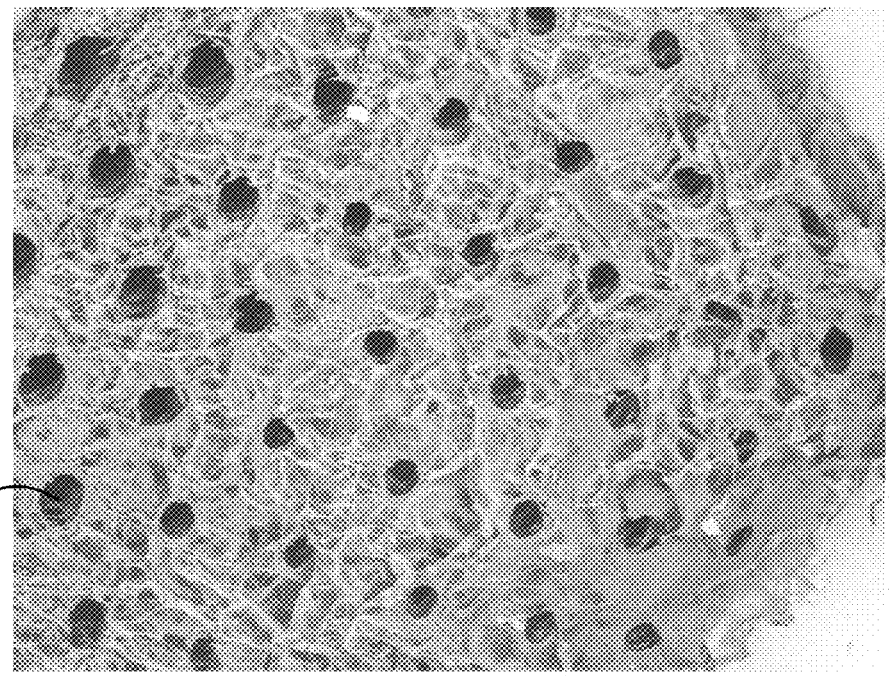
FIG. 6 illustrates the porous tissue engineering scaffold of FIG. 3 further including additional cut thru-passages.
Figure 5:
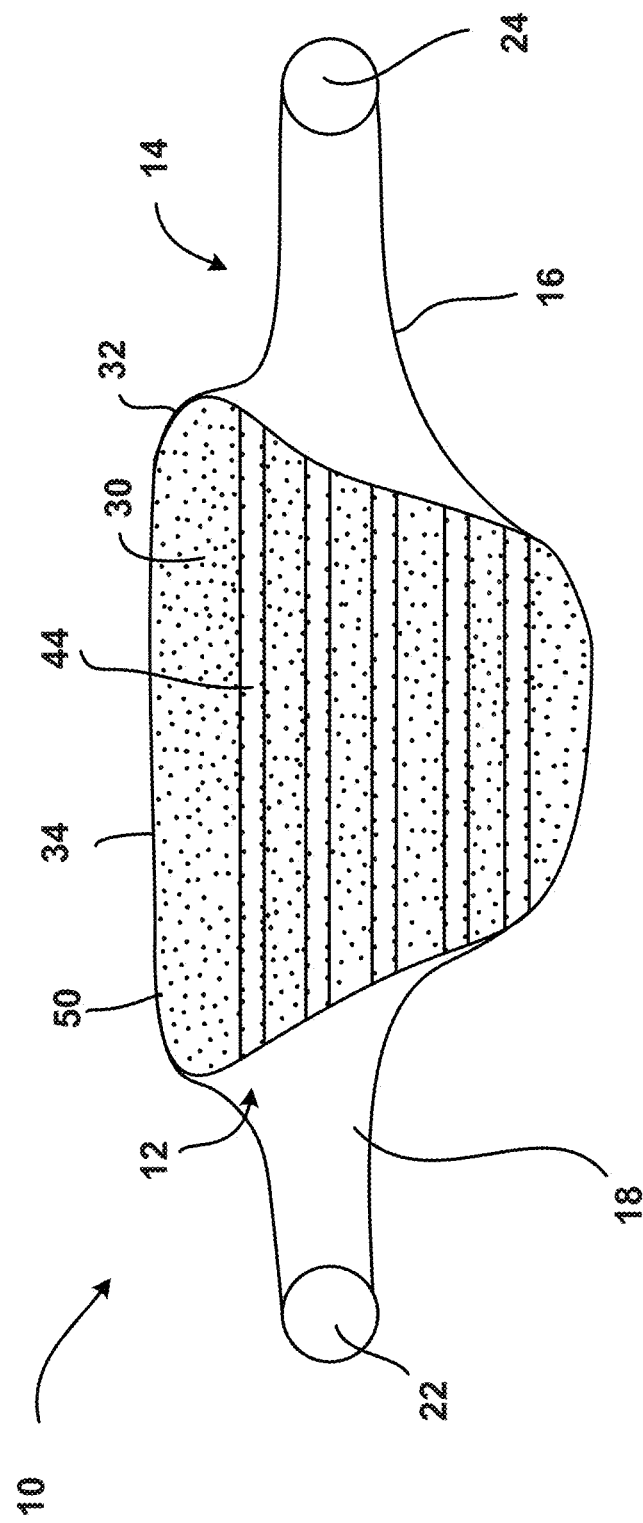
FIG. 5 illustrates the engineered tissue implant according to FIG. 2 including cells which have been added to the scaffold.

As shown in FIGS. 5 and 6, in addition to the scaffold 30 comprising a porous structure including interconnected pores, scaffold 30 may include discrete, micro sized, cut passages 44 in addition to the porous structure 32 to further enhance perfusion of a perfusion fluid through scaffold 30. The passages 44 may be linear thru holes in the scaffold 30, cut with an ultraviolet laser, drill or other cutting apparatus.

The cut passages 44 may have a diameter in the range of and including all increments between 1.0 microns (micrometers) to 10 millimeters. More particularly a diameter in the range of and including all increments between 5 microns to 200 microns. Even more particularly, the cut passages 44 may have a diameter of 100 microns.

Adjacent passages 44 may be spaced at a distance from one another of less than or equal to 600 microns to better ensure sufficient oxygen diffusion to cells within the scaffold 30 from a perfusion fluid. More particularly, passages 44 may be spaced at a distance from one another of less than or equal to 500 microns, such as in a range of and including all increments between 100 microns to 500 microns.

Among other characteristics, tubular member 14 and/or scaffold 30 may be bio-compatible, bio-degradable and bio-absorbable and finally to be integrated with a host. Additionally, tubular member 14 should be semi-permeable. All of such may be particularly provided by decellularized porcine small intestine submucosa (SIS).

As used herein, tubular member 14 and scaffold 30 may be bio-compatible with the host if, for example, such do not cause adverse effects to living tissue of the host upon implantation of engineered tissue implant 10 and permit the host to function without any adverse effects harmful to living tissue of the host.

As used herein, tubular member 14 and scaffold 30 may be bio-degradable by the host if, for example, such is at least partially degradable into molecules of lower molecular weight by biological agents of the host within a predetermined period of time, particularly at a rate corresponding with new tissue formation at a tissue reconstruction site, such as a wound site.

As used herein, tubular member 14 and scaffold 30 may be bio-absorbable by the host. In many cases the tissues need only the temporary presence of a biomaterial to support, augment or replace tissue or to guide their re-growth. Bio-absorbable materials can retain their tissue-supporting properties for a given lengths of time (typically days, weeks, or months) and they are gradually degraded biologically into tissue compatible components or absorbed by living tissues and replaced by healing tissues.

As used herein, tubular member 14 may be semi-permeable if, for example, such allows some, but not all, molecules/substances/particles of the host to pass through it and promote tissue in-growth (from surrounding tissue to the implant tissue), out-growth (from implant tissue to surround tissue), and the final integration of both to achieve wound healing.

As shown in FIG. 5, before or after introducing scaffold 30 into tubular member 14, cells 50 may be introduced to and seeded on scaffold 30. Introduction and seeding of cells 50 to scaffold 30 may be performed by applying a suspension fluid to the scaffold 30 containing the cells 50, after which a cell construct is formed. As discussed in greater detail below, cells 50 may comprise of, for example, endothelial, fibroblast and stem cells, that are required for tissue vascularization and the development into specific tissue type.

Figure 7:
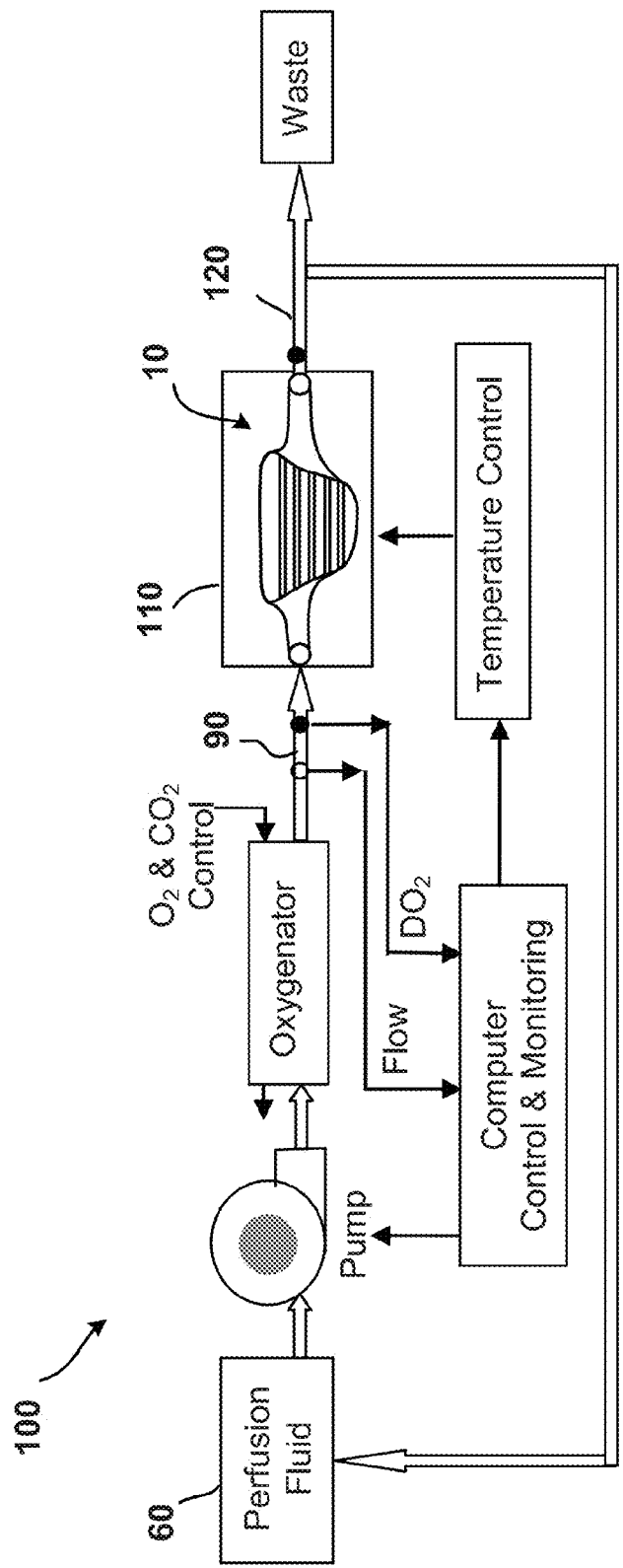
FIG. 7 illustrates an engineered tissue implant according to the present disclosure with a bioreactor apparatus.

As shown in FIG. 7, after introducing cells 50 to scaffold 30, engineered tissue implant 10 may be connected with an in vitro bioreactor apparatus 100. The flexible perfusion chamber 12 provided by tubular member 14 may serve as a flexible culture vessel in the bioreactor apparatus 100. As shown, engineered tissue implant 10 may be placed in a rigid perfusion chamber 110, and placed in fluid communication with a perfusion fluid 60.

More particularly, the fluid inlet opening 22 to fluid flow passage 18 of tubular member 14 may be connected to and in fluid communication with a fluid input passage 90 to provide the perfusion fluid 60 to engineered tissue implant 10, while the fluid outlet opening 24 to fluid flow passage 16 of tubular member 14 may be connected to and in fluid communication with a fluid output passage 120 to expel perfusion fluid 60 from engineered tissue implant 10 after such has flowed or otherwise passed through scaffold 30. After being expelled from engineered tissue implant 10, perfusion fluid 60 may be recirculated to a reservoir. Perfusion fluid 60 may include one or more nutrients and oxygen to support the metabolism of cells and otherwise sustain cells 50. In another embodiment of the disclosure, cells 50 may be first introduced and seeded to scaffold 30 from perfusion fluid 60.

Cells 50 may proliferate within the scaffold 30 under continuous perfusion. Cells 50 may also remodel the scaffold 30 and secrete extracellular matrix (ECM) within the scaffold 30. As a result of remodeling of the engineered tissue implant 10 by the cells 50, the passages provided by the porous structure and/or cut passages 44 in the scaffold 30 may become occluded by the ECM produced by cells 50. This may inhibit perfusion fluid 60 from flowing through of the engineered tissue implant 10. Consequently, it may be necessary to vascularize the engineered tissue implant 10 to provide a longer term supply of perfusion fluid 60 to cells 50 in the scaffold 30 in vitro.

Formation of a capillary network in a scaffold may be performed through angiogenesis and vasculogenesis. Endothelial cells may play a major role to form the lumen of the capillaries. In normal state, endothelial cells may be in quiescent state. However, in an activated state, such as during wound healing, inflammation, or ischemia, endothelial cells may change their phenotype to initiate angiogenesis. Growth factors like vascular endothelial growth factor (VEGF) and basic fibroblast growth factor (bFGF) may represent the most important chemical signals stimulating the vascularization process. Capillaries have been induced inside collagen, tricalcium phosphate, and PLGA scaffolds through the coculture of endothelial cells and mesenchymal stem cells with the stimulation of growth factors. Mesenchymal stem cells may not only secrete vascularization growth factor to promote vascularization, but also differentiate to pericytes to make the vascularization stable and enable maturation.

Figure 8:
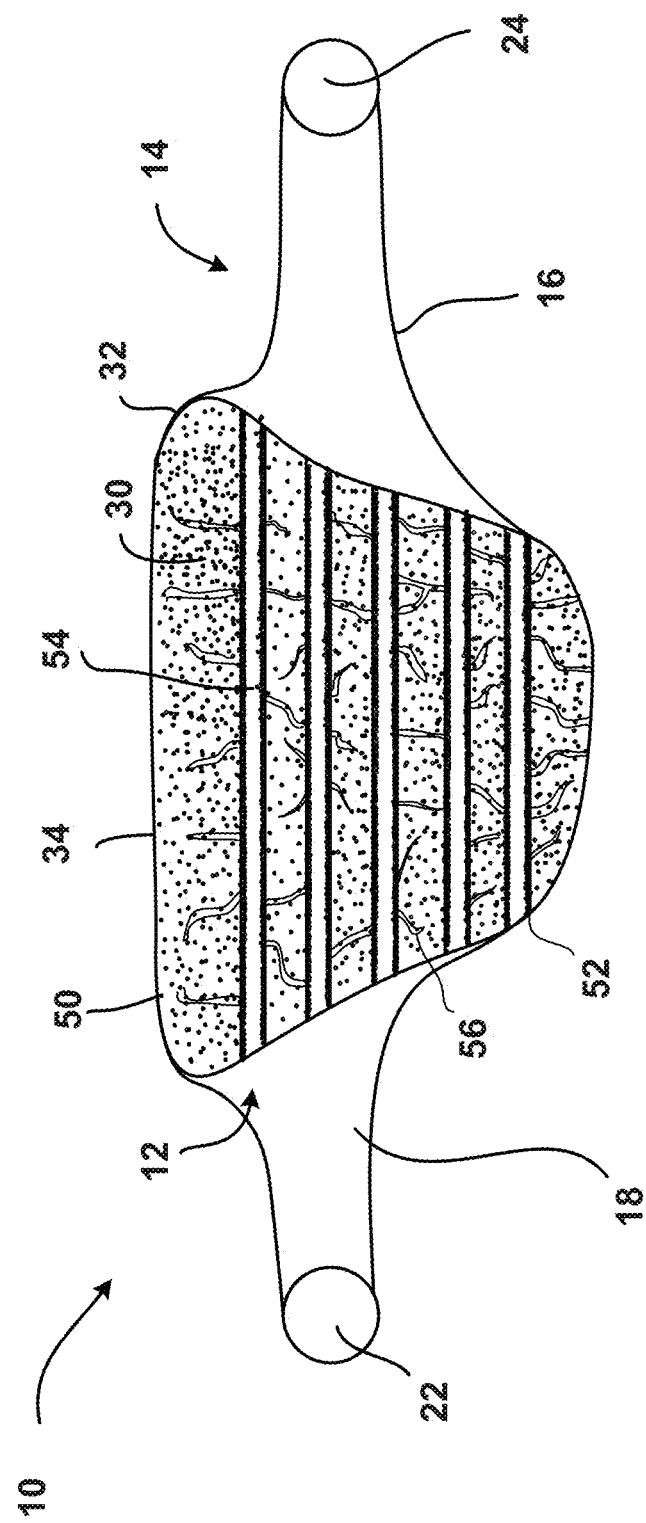
FIG. 8 illustrates an engineered tissue implant according to the present disclosure further including blood vessels formed therein.

As shown in FIG. 8, cells 50 may comprises a co-culture of endothelial cells and mesenchymal stem cells with a supplement of mechanical (e.g. shear force) and biochemical (e.g. growth factors like vascular endothelial growth factor (VEGF) and fibroblast growth factor 2 (FGF2)) signals. Cells 50 may create a lining 52 on cut passages 44 which ultimately define a wall for blood vessels 54. The formation of blood vessels stabilizes the cut passages 44 and prevents them from clotting by ECMs created by cells 50. Furthermore, cells 50 may proliferate within the porous structure of the scaffold 30 which ultimately define a wall for smaller blood vessels 56 which sprout from blood vessels 54 through angiogenesis and interconnect blood vessels 54 to provide an interconnected network of blood vessels 54, 56. The formation of blood vessels also reduces the problem thrombi formation during in vivo blood formation.

The network/system of blood vessels 54, 56 may supplement a flow of perfusion fluid 60 through the porous structure and/or passages 18 and 16 in the scaffold 30. Cells 50 including endothelial cells and mesenchymal stem cells may also create a lining on the surface of tubular member 14 and thus result in a less thrombogenic surface. In addition, the lining created by cells 50 improves the overall biocompatibility and may promote the integration of engineered tissue implants 10 to the host tissue.

Umbilical vein endothelial cells (UVECs), such as human umbilical vein endothelial cells (HUVECs), and mesenchymal stem cells (MSCs), such as human mesenchymal stem cells (hMSCs), may be obtained from Lonza (Walkersville, Md.) and isolated from the bone marrow mononuclear cells, respectively. Human umbilical vein endothelial cells (HUVECs) and human bone marrow mesenchymal stem cells (hMSCs) may be mixed at a 4:1 ratio. The mixed cells 50 may be co-cultured in an endothelial growth medium 2 (EGM-2) and then loaded to scaffold 30 of engineered tissue implant 10. The cells 50 may also comprise of adipose stem cells that have shown to contain both endothelial cells and mesenchymal stem cells.

Co-culture of human umbilical vein endothelial cells (HUVECs) and human mesenchymal stem cells (hMSCs) may provide an environment to promote hMSCs to differentiate into pericytes to stabilize and maturate the blood vessels, such as capillaries. Alternatively, human mesenchymal stem cells (hMSCs) may be pre-induced into pericytes. For example, before mixing with human umbilical vein endothelial cells (HUVECs), human mesenchymal stem cells (hMSCs) may be grown in a standard medium supplemented with 1 ng/mL of transforming growth factor beta (TGF-$\beta$) for five days. Transforming growth factor beta (TGF-$\beta$) may be understood to be an established inducer of pericytes.

The engineered tissue implant 10 may be perfused continuously in vitro in the bioreactor apparatus 100 for several weeks. As a result, a continuous three dimensional network of HUVEC-hMSC engineered blood vessels 54, 56 may form throughout the engineered tissue implant 10. The endothelial growth medium 2 (EGM-2) may also be obtained from Lonza, which includes growth factor such as vascular endothelial growth factor (VEGF) and fibroblast growth factor (FGF) to stimulate the vascularization process.

The inclusion of growth factors in perfusion fluid 60 may not be able to achieve a sustained release profile of the growth factor to maintain vascularization. Consequently, an alternative method may be to use heparin mediated release. Heparin may bind to various growth factors and release them in response to cellular activities. Heparin also may allow prolonged presentation of these growth factors by protecting them from proteolytic degradation. As an alternative method, heparin may be used to coat a scaffold 30, such as collagen. The heparinized collagen scaffold 30 may then be incubated with growth factor such as vascular endothelial growth factor (VEGF) and fibroblast growth factor (FGF) before the seeding of human umbilical vein endothelial cells (HUVECs) and human mesenchymal stem cells (hMSCs) on the engineered tissue implant 10.

Several assays may be used to monitor and evaluate the vascularization of the engineered tissue implant 10 in vitro. The first assay may be a live cell imaging microscope. Human umbilical vein endothelial cells (HUVECs) and human bone marrow mesenchymal stem cells (hMSCs) may be pre-labeled with two different-color fluorescent dyes or fluorescent proteins before mixing them together. The vascularization process can be recorded with time-lapse microscopic imaging.

A second assay may be immunohistochemistry staining. Blood vessel lumens may be demonstrated by the CD31 immunoperoxidase (antibody) stain in a histology section. Histology sections may be obtained from a scaffold 30 in different directions to determine if the vascularization is distributed uniformly inside the scaffold 30.

A third assay may be the standard hematoxylin and eosin stain (H&E) stain, which may be used to illustrate the formation of the blood vessel (capillary) network/system and the cells distributed around the blood vessels (capillaries).

Thus, as provided above, blood vessels 54 may be at least partially formed in the passages 44 of scaffold 30. More particularly, the lumen defined by passage 56 may be stabilized by the endothelial cells and pericytes to form a blood vessel (capillary system) inside the scaffold 30 during the vascularization process.

Figure 9:
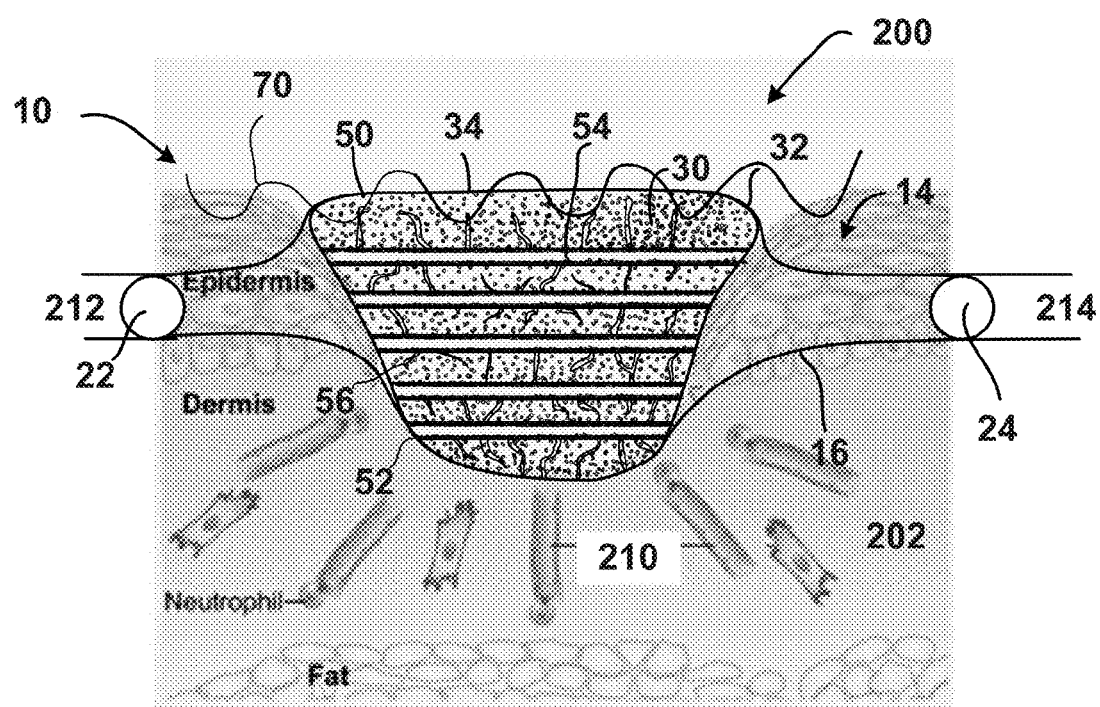
FIG. 9 illustrates an engineered tissue implant implanted in a host at a tissue reconstruction site.

As shown in FIG. 9, when the vascularized engineered tissue implant 10 is transplanted to a tissue reconstruction site 200, such as a wound site, the implant may first be reshaped to better conform to the tissue reconstruction site. Thereafter, the tubular member 14 may be connected (cannulated) with host vasculature/vessels 210 near the tissue reconstruction site 200 to form an arteriovenous (AV) loop. More particularly, fluid inlet 22 may be in fluid communication with an artery 212 and fluid outlet 24 may be in fluid communication with a vein 214. In the foregoing manner, an oxygen-rich blood supply from artery 212 is able to reach cells 50 in the scaffold 30 immediately after implantation of engineered tissue implant 10 through tubular passage 18, and the porous structure and passages 44 which may include blood vessels 54, 56 established inside the scaffold 30.

Furthermore, to better ensure contact between the cell construct 10 and the host tissue at the wound site, the cell construct 10, and in particular the tubular member 14, may be sutured to the host tissue with a suitable suture 70.

The biocompatible, semi-permeable, and degradable natural of the engineered tissue implant 10 may allow active interactions between the engineered tissue implant 10 and surrounding living tissue 202 and vasculature 210 so that the engineered tissue implant 10 is able to completely integrate into the surrounding tissue 202 as the tissue reconstruction site 200 heals.

For example, a physiological response of the host to a presence of the engineered tissue implant 10 may be used to either at least partially degrade and/or absorb the tubular member 14 by the host. As a result, when the tubular member 14 is sufficiently degraded and/or absorbed by the host, blood vessels of the engineered tissue implant 10 and/or blood vessels of the host may then proliferate across a boundary of the implant and the host, which may be defined by a prior location of the tubular member 14. In other words, when the tubular member 14 has been at least partially degraded and at least partially absorbed by the host such that the blood vessels may cross the boundary. At that time, a new vascular network is formed between the engineered tissue implant 10 and the host, and the arteriovenous (AV) loop may be disconnected. It should also be appreciated that absorbtion may occur by tissue in-growth into the implant or tissue out-growth from the implant.

Figure 10:
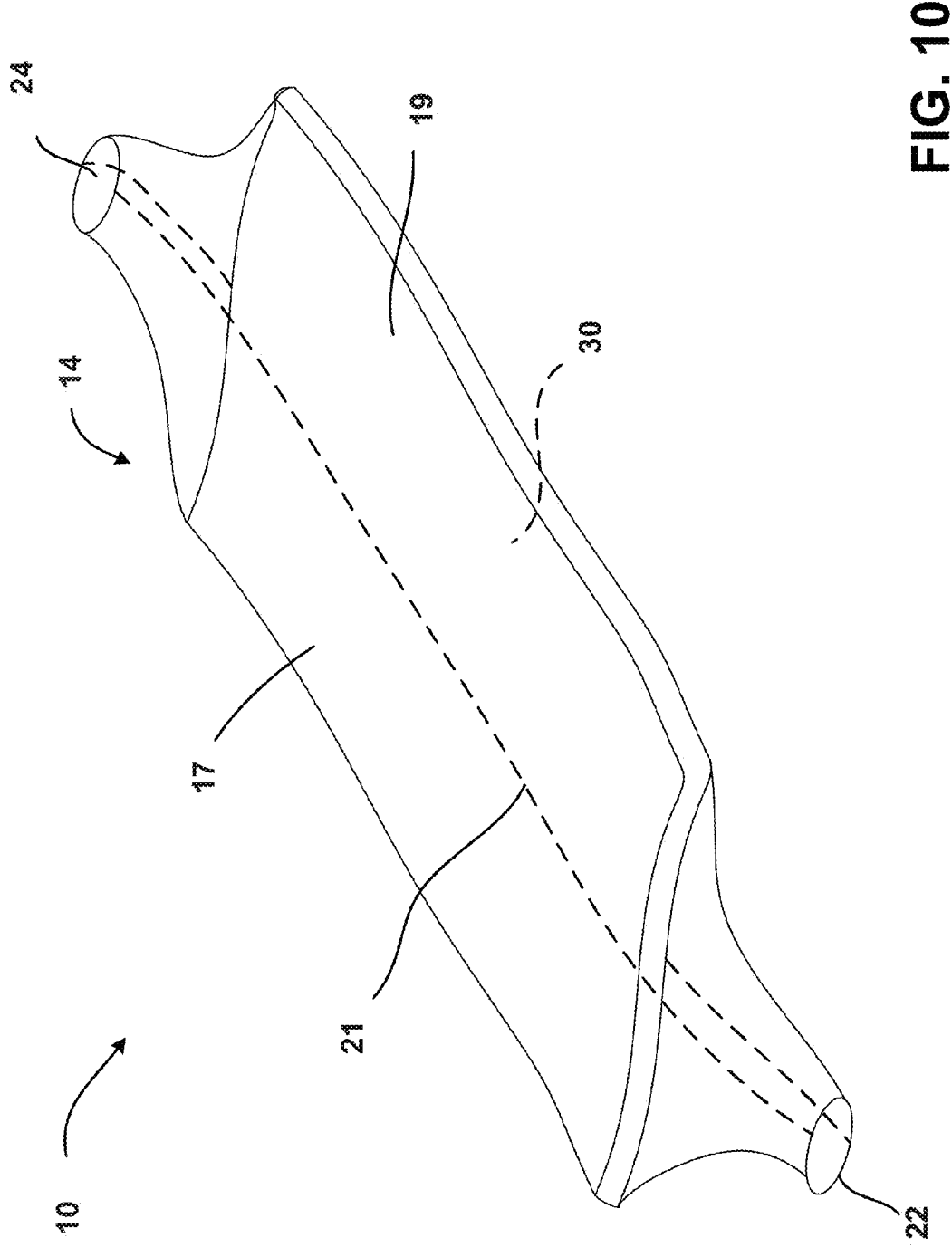
FIG. 10 illustrates another embodiment of an engineered tissue implant according to the present disclosure.

Another engineered tissue implant 10 according to the present disclosure is shown at FIG. 10, in which engineered tissue implant 10 is planar. In certain instances, due to a large planar nature of engineered tissue implant 10 and the corresponding size of tubular member 14, it may be necessary to shrink the tubular member 14 at the ends thereof adjacent scaffold 30, for example, with suture or adhesive to reduce the size of the fluid inlet opening 22 and fluid outlet opening 24 of the tubular member 14 and reduce the cross-sectional area thereof as compared to the cross-sectional area of the tubular member 14 occupied by scaffold 30. In this manner it may be easier to connect the fluid inlet opening 22 and fluid outlet opening 24 to the host.

Also, tubular member 14 may be formed by one or more pieces/sections 17, 19 with one or more joint lines 21 extending longitudinally with tubular passage 14. Sections 17, 19 forming joints 21 may be connected by, for example, a suture or adhesive. Multiple sections 17, 19 of tubular member 14 may be necessary depending upon the size of scaffold 30, such as for a large scaffold 30.

Advantageously, the flexible perfusion chamber provided by tubular member 14 may be conformable to fit different shapes and materials of scaffolds 30. Therefore, the scaffold 30 can be configured to fit the sites of tissue damage to optimize the wound treatment. This engineered tissue implant 10 may also provide a functional extracellular matrix (developed in vitro) transplanted to the wound sites that may achieve faster and better wound healing. The engineered tissue implant 10 may provide a perfusion chamber connectable to the vasculature of the host. The tissue reconstruction 10 may include an internal vasculature, particularly in the form of a capillary network/system, to deliver blood and oxygen supplies to a wound site that are important to the tissue reconstruction/wound healing process. This transplantable engineered tissue implant 10 may be used as an alternative autograft or allograft tissue used for free flap reconstruction.

What is claimed is:

1. A method to provide tissue for reconstruction comprising:
   providing a perfusion chamber formed with a biodegradable flexible tubular member having a wall defining a fluid flow passage, a fluid inlet opening and a fluid outlet opening, and composed of a decellularized human or animal tubular body passage; and
   inserting and positioning a porous three-dimensional scaffold within the fluid flow passage of the biodegradable flexible tubular member through the fluid inlet opening or fluid outlet opening, the porous scaffold comprising pores and passageways for developing vascular tissue;
   arranging the tubular member with the porous scaffold such that, in a presence of a perfusion fluid, the perfusion fluid will flow through the porous scaffold including the passageways and be inhibited from flowing between the porous scaffold and the wall of the tubular member;
   introducing and seeding mesenchymal stem cells into the scaffold;
   introducing a perfusion fluid to the scaffold which flows through the fluid flow passage and porous scaffold including the passageways;
   proliferating the cells within the scaffold; and
   forming at least a first tissue type selected from muscle, bone, cartilage and epithelial, said tissue including extracellular matrix and blood vessels within the porous scaffold so as to produce an implant having a vascularized cohesive tissue contained within the tubular member.

2. The method of claim 1 wherein said seeding the cells further comprises seeding at least one of endothelial cells, and fibroblast and further adding vascular growth factor.

3. The method of claim 1 wherein:
the perfusion fluid includes one or more nutrients and oxygen to sustain the cells.

4. The method of claim 1 wherein the blood vessels include a capillary network.

5. The method of claim 1 wherein:
the passageways are defined by interconnected pores forming a fluid path in the porous structure of the scaffold.

6. The method of claim 1 wherein further comprising:
cutting tubular thru-holes in the scaffold to provide the passageways in the scaffold.

7. The method of claim 1 wherein:
the blood vessels form an interconnected network.

8. The method of claim 1 further comprising:
secreting components of extracellular matrix from the cells within the scaffold.

9. The method of claim 1 further comprising:
introducing the implant to a tissue reconstruction site of a host.

10. The method of claim 9 further comprising:
attaching a fluid inlet to the fluid flow passage of the tubular member to an artery of a host and receiving a flow of blood from the artery into the fluid flow passage.

11. The method of claim 10 further comprising:
attaching a fluid outlet to the fluid flow passage of the tubular member to a vein of the host and expelling the blood in the fluid flow passage received from the artery to the vein.

12. The method of claim 10 further comprising:
passing the flow of blood through the blood vessels within the scaffold after receiving the flow of blood from the artery into the fluid flow passage.

13. The method of claim 9 further comprising:
shaping the implant to increase a conformance of the implant to a shape of the tissue reconstruction site of the host.

14. The method of claim 9 further comprising:
mechanically attaching the implant to the host.

15. The method of claim 14 wherein:
mechanically attaching the implant to the host comprises suturing the implant to the host.

16. The method of claim 15 wherein:
suturing the implant to the host comprises suturing the flexible tubular member to the host.

17. The method of claim 9 wherein:
the tubular member has been at least one of at least partially degraded and at least partially absorbed by the host.

18. The method of claim 1 wherein:
the tubular body passage is selected from intestinal track or blood vessel.

19. The method of claim 1 further comprising:
arranging the tubular member with the porous scaffold such that the tubular member provides a compression fit around the porous scaffold to inhibit the perfusion fluid from flowing between the porous scaffold and the wall of the tubular member.

20. The method of claim 1 further comprising:
arranging the tubular member with the porous scaffold such that the tubular member and the porous scaffold are mechanically joined to inhibit the perfusion fluid from flowing between the porous scaffold and the wall of the tubular member.

21. The method of claim 20 wherein:
the tubular member and the porous scaffold are mechanically joined by a suture.

22. The method of claim 1 further comprising:
arranging the tubular member with the porous scaffold such that the tubular member and the porous scaffold are bonded together to inhibit the perfusion fluid from flowing between the porous scaffold and the wall of the tubular member.

23. The method of claim 22 wherein:
the tubular member and the porous scaffold are bonded by an adhesive.

* * * * *